United States Patent [19]

Berger

[11] Patent Number: 5,008,293

[45] Date of Patent: Apr. 16, 1991

[54] PROCESS FOR THE TREATMENT OF THE SKIN TO ALLEVIATE SKIN DISEASES ARISING FROM CONTACT SENSITIZATION OR IRRITATION UTILIZING P-SUBSTITUTED PHENOXY ALKANOLS

[76] Inventor: Frank M. Berger, 515 E. 72nd St., Ste. 30E, New York, N.Y. 10021

[21] Appl. No.: 223,146

[22] Filed: Jul. 22, 1988

[51] Int. Cl.$^5$ ............................................ A61K 31/075
[52] U.S. Cl. ............................. 514/718; 514/719/974
[58] Field of Search ............................... 514/718, 719

[56] References Cited

U.S. PATENT DOCUMENTS 3,839,587 10/1974 Hoffmann et al. .................. 514/718
3,954,965 5/1976 Boghosian et al. ............. 514/718 X
4,451,474 5/1984 Berger et al. ....................... 514/356

OTHER PUBLICATIONS

Martin Dale, The Extra Pharmacopoeia, 26th ed., p. 772.
Cecil Textbook of Medicine, 18th ed. pp. 2300 through 2323, 18th ed, 1988.

*Primary Examiner*—Leonard Schenkman

[57] ABSTRACT

Skin diseases are treated by topical application of p-substituted phenoxy alkanols having the structure:

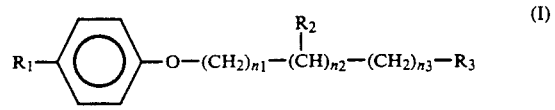

in which:
$R_1$ substituted in ortho, meta or para position is selected from hydrogen, halogen, alkyl having from one to six carbon atoms, preferably para-chlorine or para-tertiary-butyl; and bivalent cycloalkylene condensed with the phenyl group at adjacent ring carbons thereof, such as in indane;

$R_2$ and $R_3$ are hydrogen or hydroxyl and at least one of $R_2$ and $R_3$ is hydroxyl; and $N_1$, $n_2$ and $n_3$ represent the number of $CH_2$, $CHR_2$ and $CH_2$ groups, respectively, and are numbers within the range from 1 to 10.

The topical application to the skin of these compounds jointly with an agent that causes irritation, inflammation or contact sensitization modifies and mitigates such irritation, inflammation and sensitization.

8 Claims, No Drawings

PROCESS FOR THE TREATMENT OF THE SKIN TO ALLEVIATE SKIN DISEASES ARISING FROM CONTACT SENSITIZATION OR IRRITATION UTILIZING P-SUBSTITUTED PHENOXY ALKANOLS

Chlorphenesin has the structure:

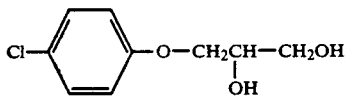

Chlorphenesin appears in the form of pale, cream-colored crystals or crystalline aggregates. It is of bitter taste. Melting point 78° to 81° C. Soluble in 1 in 200 of water, 1 in 5 of ethanol, slightly soluble in fixed oils.

Chlorphenesin was originally described as a skeletal muscle relaxant and its pharmacological properties described by Berger and Bradley (Brit. J. Pharmacol 1: 265-272, 1946). Bradley and Forrest obtained a patent describing the preparation of chlorphenesin (British patent No. 628, 497, 1949). Subsequently it has been shown that chlorphenesin possesses antibacterial and antifungal properties (Berger et al, *Journal of Applied Microbiology* 1: 146-149, 1953). The drug has been commercially available in Great Britain, and sold under the trade name Mycil by the British Drug Houses as a topical antifungal agent. The drug is listed the *British Pharmacopeia* 1973.

The biological properties of chlorphenesin have been explored by a number of investigators. Lichtenstein and Adkinson demonstrated that chlorphenesin inhibits histamine release from human leukocytes (*J. Immunology* 103: 866, 1969).

Berger, Fukui, Goldenbaum, DeAngelo and Chandlee, *The Journal of Immunology* 102 1024 (1969), reported the effect of the drug on immune responses. Chlorphenesin when given jointly with the antigen suppressed antibody formation. The drug also had an effect on delayed hypersensitivity reactions, when given at the time of challenge.

Chlorphenesin also suppressed passive cutaneous anaphylaxis induced by penicillin, according to Berger, Fukui, Ludwig and Margolin, *Proceedings of the Society for Experimental Biology and Medicine* 124 303 (1967).

Chlorphenesin also was reported to inhibit allergen-reagin-induced histamine and SRS-A release from monkey lung tissue passively sensitized with human reagin, Malley and Baecher *Journal of Immunology* 107 586 (1971).

Kimura, Inoue and Honda demonstrated that chlorphenesin and cromolyn sodium inhibited the degranulation of the rat mast cells mediated by IgE- anti-IgE reaction, and published their findings in *Immunology* 26 983 (1974).

Chlorphenesin also inhibited release of histamine induced by concanavalin A from basophil cells according to Siraganian and Siraganian, *Journal of Immunology* 112 2117 (1974).

Stites, Brecher, Schmidt and Berger showed that chlorphenesin inhibited mitogenic responses of mouse and human B and T cells induced by phytohemagglutinins, lipopolysaccharide or staphylococcal protein A. The compound also inhibited the mixed lymphocytes reactions in inbred strains of mice and in unrelated humans *Immunopharmacology* (1979).

All these results indicate that chlorphenesin has an inhibitory effect on the release of various mediator substances. Because chlorphenesin is rapidly metabolised and broken down in the body, it could not be therapeutically utilized for any of the above described applications. Numerous attempts have been made to overcome these drawbacks by changing the molecular structure of the parent compound and several U.S. patents describing new composition of matter have issued. These patents describe groups of compounds related to chlorphenesin that are far more effective in inhibiting mediator release and are more resistant to inactivation by the metabolic processes in the body.

Inai, Okazaki, Shimada, Kagei and Bessho, U.S. Pat. No. 3,846,480 patented Nov. 5, 1974, describe chlorphenesin succinate and its alkali metal salts, and indicated that these were much superior to chlorphenesin in their anaphylactic histamine release-preventive effect. These compounds are not being used therapeutically because of inadequate clinical and pharmacological potency.

Reisner, Ludwig, Fukui and Berger U.S. Pat. No. 3,879,544 patented Apr. 22, 1975 developed a group of new aryl thioalkanones having the formula:

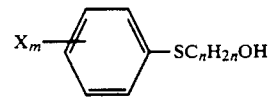

wherein X is halogen or lower alkyl; m is an integer 1 or 2 and n is an integer from 2 to 6, inclusive. As used throughout the instant specification and claims the term lower alkyl shall mean carbon chains containing 1-6 carbon atoms.

Berger, DeGraw and Johnson, U.S. Pat. Nos. 4,451,474, patented May 29, 1984 and 4,543,312, patented Sept. 24, 1985, provide p-alkyl or cycloalkyl phenoxy alkanols and esters having the structure:

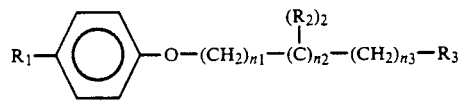

in which:

$R_1$ is an alkyl group having from one to six carbon atoms, preferably tertiary, and still more preferably tertiary-butyl; or a bivalent cycloalkylene group condensed with the phenyl group at adjacent ring carbons thereof, such as in indane;

$R_2$ is lower alkyl having from one to three carbon atoms or hydrogen;

$R_3$ is hydroxyl or an ester group selected from the group consisting of $COOR_4$ and $OOCR_4$ derived from unsubstituted and hydroxy-substituted monocarboxylic acids and $COOR_5OOC$ and $OOCR_5COO$ derived from unsubstituted and hydroxy-substituted dicarboxylic acids, the acids being selected from the group consisting of aliphatic acids, including carbamic acid, having from one to about twelve carbon atoms; cycloaliphatic acids having from three to about twelve carbon atoms; carbocyclic aromatic acids having from six to about twenty carbon atoms; and nitrogen heterocyclic aromatic acids having from five to about twelve carbon atoms, $R_4$ being monovalent aliphatic, cycloaliphatic, aromatic, or nitrogen heterocyclic aromatic, and $R_5$ being divalent aliphatic, cycloaliphatic, aromatic, or nitrogen heterocyclic aromatic, the acids being esterified with aliphatic alcohols having from one to six carbon atoms; and carbonic acid monoalkyl esters, the alkyl having from one to three carbon atoms; and $n_1$, $n_2$ and $n_3$ represent the number of $CH_2$, $C(R_2)_2$ and $CH_2$ groups, respectively, and are numbers within the range from 0 to 10; and at least one of $n_1$, $n_2$ and $n_3$ is other than zero.

These compounds are said to inhibit abnormal tissue reactivity due to specific allergic hypersensitivity or due to specific irritants by inhibiting the release of chemical mediators that are responsible for the symptoms of allergic diseases, including allergic rhinitis, asthma, hypersensitivity of the skin and of the gastrointestinal canal, and the many symptoms of irritation and inflammation produced by irritants and inflammation-causing substances.

In work unrelated to allergic reactions, Berger and Fukui U.S. Pat. No. 3,549,766 patented Dec. 22, 1970 described a method of eliminating or reducing hypersensitivity to penicillin by administering in conjunction with the penicillin, certain phenoxy propanols or phenoxypropanediols having the structure:

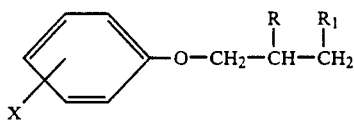

wherein X is selected from the group consisting of hydrogen, halogen, lower alkyl and lower alkoxy; and R and $R_1$ are each selected from the group consisting of hydrogen and hydroxyl, at least one being hydroxyl.

As used herein and in the appended claims, the terms "lower alkyl" and "lower alkoxy" signify respectively alkyl and alkoxy radicals having from one to about six carbon atoms.

This group includes chlorphenesin, in the case when X is Cl and R and $R_1$ are each OH. Nothing in the patent suggests possible utility of phenoxy propanols or diols alleviating skin diseases arising from contact sensitization or irritation.

In a contemporaneous paper, Berger and Fukui, *Giornale dell'Arteriosclerosi* V No. 5—Sept.-Oct. 1967 describe the effect of the phenoxy propanediols in decreasing the penicillin-induced passive anaphylaxis reaction, with particular emphasis on chlorphenesin, 3-p-chlorophenoxy-1,2-propanediol. In the summary at the end of the paper, the authors comment:

These observations appear to be of particular interest because the mode of action of these compounds appears to be entirely different from that of previously described inhibitors of anaphylactic reactions. The phenoxypropanediols do not destroy penicillin and do not affect its antibiotic action. They are devoid of antihistaminic and anti-inflammatory properties and do not act by depressing the general reactivity of the organism. The compounds appear to act by a selective blocking of certain antibody sites, thus making the antibody unable to react with penicillin. This effect is of particular interest because of its specificity. The action of phenoxypropanediols on cutaneous anaphylaxis may open up new approaches to the treatment of hypersensitivity and autoimmune diseases.

A corresponding report by Berger, Fukui, Ludwig and Margolin appeared in *Proc. of the Society for Exp. Biology and Medicine* 124 303-310 (1967), and the same conclusion is reached at page 310.

All the pharmacological properties of chlorphenesin described in the published material up to the present depend on the inhibition of the release of histamin and other mediators of allergic reactions, sometimes also called reaginic reactions. All allergic and reaginic reactions are known to be mediated by the Immunoglobulin IgE and the effects of chlorphenesin described in the above mentioned literature and patents have been explained by inhibiting the IgE mediated mediator release.

It is therefore unexpected and surprising to note that chlorphenesin and closely related compounds of the genus of Formula I if applied topically to the skin will alleviate contact hypersensitivity, which is a cell-mediated response in which immunoglobulin IgE plays no part.

This novel property of these compounds is demonstrated when the compound is administered topically to the skin jointly with an agent that causes irritation or contact sensitization. The compound is effective not only when first applied with the irritant, but on subsequent applications together with the irritant or sensitizing agent also effectively modifies and mitigates irritation.

The compounds in accordance with the invention are o-, m- or p-substituted phenoxy alkanols having the general formula:

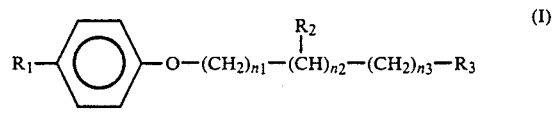

in which:

$R_1$ substituted in o-, m- or p-position or combination of these is selected from hydrogen, halogen, alkyl having from one to six carbon atoms, preferably chlorine substituted on the benzene ring in position 2, 3 or 4 or tertiary-butyl substituted on the benzene ring in position 2, 3 or 4; and bivalent cycloalkylene condensed with the phenyl group at adjacent ring carbons thereof, such as in indane;

$R_2$ and $R_3$ are hydrogen or hydroxyl and at least one of $R_2$ and $R_3$ is hydroxyl; and $n_1$, $n_2$ and $n_3$ represent the number of $CH_2$, $CHR_2$ and $CH_2$ groups, respectively, and are numbers within the range from 1 to 10.

The topical application to the skin of these compounds jointly with an agent that causes irritation or contact sensitization modifies and mitigates such irritation and sensitization.

Exemplary $R_1$ halogen substituents are fluorine, chlorine, bromine and iodine.

Exemplary $R_1$ alkyl substituents include methyl, ethyl, propyl, isopropyl, butyl, isobutyl, secondary-butyl, tertiary-butyl, amyl, secondary-amyl, tertiary-amyl, hexyl, secondary-hexyl, and tertiary-hexyl.

Exemplary $R_1$ cycloalkylene substituents include cyclopropylene, cyclobutylene and cyclopentylene, forming five, six and seven membered carboxylic rings with the phenyl, as in indane and tetrahydroquinoline.

A number of preferred compounds falling within the invention are illustrated in Table I.

TABLE I

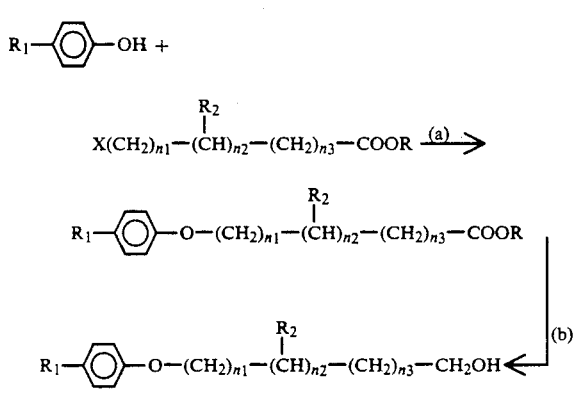

| $R_1$ | $-O-(CH_2)_{n1}-(CH)_{n2}-(CH_2)_{n3}-R_3$ with $(R_2)_2$ on $(C)_{n2}$ |
|---|---|
| Chlorphenesin | $-O-CH_2.CHOH-CH_2OH$ |
| 4-chloro | |
| 4-chloro | $-O-CH_2.CHOH.COOH$ |
| 4-bromo | $-O-CH_2.CH_2.CH_2OH$ |
| 4-n-propyl | $-O-CH_2.CH_2OH$ |
| 4-tertiary-butyl | $-O-CH_2.CH_2OH$ |
| 4-isopropyl | $-O-CH_2.CH_2.CH_2OH$ |
| 4-n-propyl | $-O-CH_2.CH_2.CH_2OH$ |
| 4-isobutyl | $-O-CH_2.CH_2.CH_2OH$ |
| 4-tertiary-butyl | $-O-CH_2.CH_2.CH_2OH$ |
| 4-sec-butyl | $-O-CH_2.CH_2.CH_2OH$ |
| 4-pentyl | $-O-CH_2.CH_2.CH_2OH$ |
| Cyclobutylene (Indane) | $-O-CH_2.CH_2.CH_2OH$ |
| 4-n-propyl | $-O-CH_2.CH_2.CH_2.CH_2OH$ |
| 4-tertiary-butyl | $-O-CH_2.CH_2.CH_2.CH_2OH$ |
| 4-n-propyl | $-O-CH_2.CH_2.CH_2.CH_2$ |
| 4-n-propyl | $-O-CH_2.CH_2-C(CH_3)_2OH$ |

The compounds of Formula I can be made by any of three general syntheses:

Synthesis A

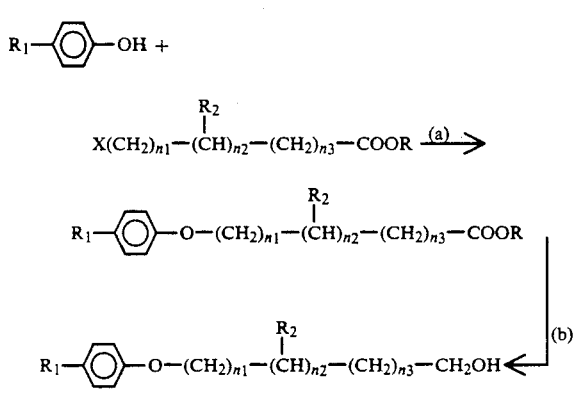

This route involves in step (a) reaction of a phenol having the $R_1$ substituent of Formula I, with an ester or acid corresponding in structure to the

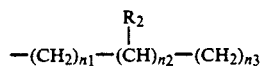

substituent, having a group X that is suitably activated for displacement by a phenoxide ion at the position where the group is to be linked to the phenolic hydroxyl group. The reaction requires ionization of the phenolic substrate with a suitable base, such as an alkali metal hydride, an alkali metal hydroxide, carbonate or alkoxide, or an organic base such as a tertiary amine, for instance, triethyl amine, pyridine, or a quaternary ammonium hydroxide such as tetramethyl ammonium hydroxide, in an inert organic solvent, such as a polar solvent.

The reaction proceeds at room temperature up to a moderately elevated temperature within the range from about 25° to about 150° C.

The COOR group is an ester derived from the acid COOH esterified with an alcohol, such as the alkanols, in which case R is an alkyl group, such as methyl, ethyl, propyl and butyl; an aryl group derived from a phenol, such as phenyl and naphthyl; an alkaryl group derived from an aryl alcohol, such as benzyl and phenethyl; and a cycloalkyl group derived from a cycloalkanol, such as cyclohexyl and cycloheptyl.

X represents the activated substituent, and is preferably halogen selected from the group consisting of chlorine, bromine and iodine, but sulfonyloxy groups can also be used.

The $n_1$, $n_2$ and $n_3$ substituents correspond of course to the like substituents of Formula I, as also does the $R_1$ substituent on the phenol.

In step (b) of this reaction, the phenoxy alkylene ester is reduced with a metal hydride, such as lithium aluminum hydride, diisobutyl aluminum hydride, or other hydrides, or a borane, converting the ester COOR group to a $CH_2OH$ group, in the presence of an inert organic solvent that is compatible with and inert to strong reducing agents. Ethers, such as diethyl ether, tetrahydrofuran, dioxane, and dimethoxyethane can be used, as well as hydrocarbons such as toluene, which may be favored with the alkyl metal hydrides.

Synthesis B

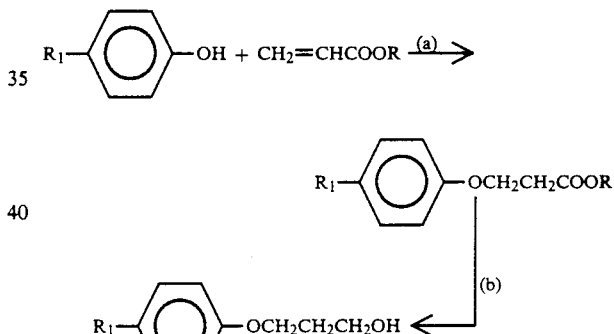

In step (a) of this procedure, a phenol

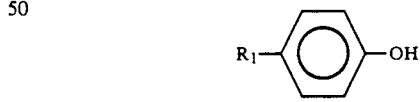

having a para substituent corresponding to $R_1$ is employed together with a lower acrylic acid ester, which following reduction in step (b) produces a substituent corresponding to the

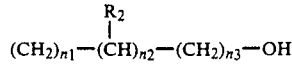

substituent of Formula I.

The reaction between the phenol and the lower acrylate ester requires ionization of the phenolic substrate with a suitable base, such as a metal hydride, alkali metal hydroxide, carbonate, or alkoxide, or a suitable organic base, as in Synthesis A, but it can also be carried out with only a catalytic quantity of the base, and in the absence of an inert organic solvent. The R substituent on the acrylic acid can be alkyl, aryl, alkaryl or cycloalkyl, but in this case better yields are obtained when R is of a higher molecular weight than methyl or ethyl, such as, for example, butyl.

The higher acrylate esters have higher boiling points, and it is likely, if the reaction is carried out under reflux, that the higher boiling point of the acrylate ester influences the reaction, with the best yields being obtained when the acrylate ester has a boiling point above 100° C.

In step (b) of this reaction, the COOR ester group is reduced to $CH_2OH$, as in Synthesis A, and a similar procedure can be used.

Synthesis C

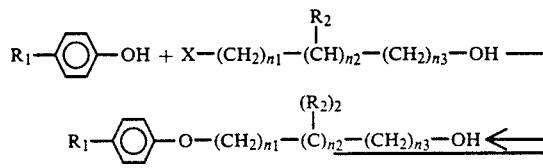

This synthesis also requires ionization of the phenolic substrate with a suitable base, preferably in an inert organic solvent as in Synthesis A, followed by alkylation with a suitable halogen-substituted or sulfonate ester-substituted alcohol or ester having a structure corresponding to the

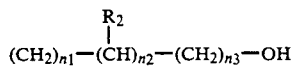

group, where OR is $R_3$ of Formula I.

The X group is suitably activated for displacement by a phenoxide ion, and can be any of the X groups of the esters in Synthesis A.

In the case where the alkylene substituent has two, four and five carbon atoms, $R_3$ is preferably an ester group, but in other cases $R_3$ can be either hydrogen or an ester group. At the particular chain length where the substituent has two, four and five carbon atoms, the cyclization of the reagent to ethylene oxide, tetrahydrofuran or tetrahydropyran is competitive with alkylation of the phenoxide, reducing the yield, unless the hydroxyl group is protected by esterification. Thus, when the number of carbon atoms in the substituent is two, four or five, the hydroxyl group should be protected by reaction with an acid, so as to form an ester, such as the acetate or propionate, the esterifying radical being removed by ordinary saponification following the alkylation.

This reaction proceeds at an elevated temperature within the range from about 25° to about 150° C., and is preferably carried out in an inert organic solvent, preferably a polar solvent.

The effectiveness of the compounds of the invention in topical application to the skin was evaluated by the following experiment, using chlorphensin to block sensitization and expression of contact sensitivity in mice. The mice used were 6 to 8 weeks old of the Balb/c strain. Mice were sensitized by painting with about 50 $\mu l$ of 0.5% solution of dinitrofluorobenzene (DNFB) in acetone olive oil on two consecutive days. Four to five days later a state of specific contact sensitivity to DNFB was elicited by applying 20 $\mu l$ of 0.2% DNFB acetone olive oil solution to the ear. The swelling or thickness of the ear was measured 24 hours later with an engineer's micrometer, and expressed as $\times 10^{-4}$ inches. Control animals received acetone-oil alone on both sensitization and challenge, or were sensitized with acetone-oil and challenged with DNFB.

TABLE II

| Sensitized with | Challenged with | Control ear | Test ear | Change in ear thickness | % reduction |
|---|---|---|---|---|---|
| | First challenge | | | | |
| Acetone-oil | Acetone-oil | 0.0130 | 0.0130 | 0 | — |
| Acetone-oil | Dinitrofluorobenzene | 0.0125 | 0.0175 | 50 | — |
| Dinitrofluorobenzene | Dinitrofluorobenzene | 0.0130 | 0.0195 | 65 | — |
| Dinitrofluorobenzene | Dinitrofluorobenzene + 2% Chlorphenesin | 0.0125 | 0.0125 | 0 | 100 |
| | Second challenge | | | | |
| Acetone-oil | Acetone-oil | 0.0130 | 0.0135 | 5 | — |
| Acetone-oil | Dinitrofluorobenzene | 0.0125 | 0.0260 | 135 | — |
| Dinitrofluorobenzene | Dinitrofluorobenzene | 0.0130 | 0.0230 | 100 | — |
| Dinitrofluorobenzene | Dinitrofluorobenzene + 2% Chlorphenesin | 0.0125 | 0.0148 | 23 | 77 |

The animals were challenged twice, two days apart.

The results indicate that chlorphenesin strikingly reduced expression of DNFB sensitivity. The contact sensitivity is an expression of delayed-type hypersensitivity. It is a cell-mediated immune response that manifests itself after challenge by cellular infiltration and edema which are at their maximum 24 to 48 hours after challenge. In this type of response immunoglobulin IgE, atopic allergic or reaginic responses are not involved. While it has been previously shown that chlorphenesin inhibits various allergic responses mediated by IgE, it is unexpected and unpredictable that chlorphenesin also affects delayed-type hypersensitivity reactions that are entirely different in kind.

The p-substituted phenoxy alkanol can be administered to the animal by any available form of topical administration. The amount administered is sufficient to inhibit contact hypersensitivity due to specific irritants, in concentrations that are in no way critical, and can, for example, lie within the range from about 0.1% to about 10% w/w. This amount will depend upon the species of animal, and the weight of the animal. For example, in human topical adminstration, a dosage of the alkanol or ester compound within the range from about 2 mg to about 500 mg per application per day should be sufficient. In the treatment of lower test animals, a similar dosage range is therapeutic. The upper limit of dosage is that imposed by toxic side effects, and can be determined by trial and error for the animal to be treated, including humans.

It is not practicable to administer chlorphenesin systemically in the treatment of diseases of the skin. The reason for this is the observation that chlorphenesin is promptly broken down in the body to inactive compounds. We have found that chlorphenesin when applied to the skin is not broken down.

To facilitate administration, the p-substituted phenoxy alkanol can be provided in composition form, and preferably in dosage unit form. While the compound can be administered topically per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the p-substituted phenoxy alkanol. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propylhydroxybenzoate, talc or magnesium stearate. Other agents that can be used for solubilizing or dispersing these compounds are dimethyl sulfoxide (DMSO), N,N-dimethyl acetamide (DMAC), propylene glycol and the polyoxyethylene ethers of hexitol fatty acid esters, such as sorbitol and mannitol esterified with lauric, stearic, palmitic or oleic acids, condensed with from ten to thirty moles of ethylene oxide. A commercially available material is Tween 80, a polyoxyethylene sorbitol oleate, the oleic acid ester of sorbitol condensed with twenty moles ethylene oxide per mole of sorbitol.

For convenience, the p-substituted phenoxy alkanol and carrier or diluent can be formulated as an ointment or cream or solution, and dosage units can be encapsulated in a capsule, sachet, cachet, gelatin, paper or other container.

The following Examples illustrate various forms of therapeutic topical compositions in which the p-substituted phenoxy alkanol can be administered, exemplified by chlorphenesin:

EXAMPLE I

| Emollient cream | % by weight | |
|---|---|---|
| | A | B |
| Chlorphenesin | 15.00 | 15.00 |
| Beeswax | 15.00 | 15.00 |
| Spermaceti | 5.00 | — |
| Light mineral oil | 30.00 | 30.00 |
| Palm kernel oil (I.V. 14 to 23) | 26.00 | 16.00 |
| Hydrogenated cottonseed oil | — | 10.00 |

-continued

| Emollient cream | % by weight | |
|---|---|---|
| | A | B |
| Propyl paraben | 0.15 | 0.15 |
| Propenyl methyl guaethol | 0.05 | 0.05 |
| Methyl paraben | 0.15 | 0.15 |
| Borax | 0.50 | 0.50 |
| Water | 22.90 | 27.90 |
| Perfume | 0.25 | 0.25 |

EXAMPLE II

| Emollient cream, Nonionic O/W Type | | |
|---|---|---|
| | A | B |
| Part A | | |
| Chlorphenesin | 3.0% | 3.0% |
| Beeswax | 3.0% | — |
| Spermaceti | 3.0% | — |
| Light mineral oil | 30.0% | — |
| Glyceryl monostearate, pure | 12.0% | 4.5% |
| Lanolin | — | 1.0% |
| Isopropyl myristate | — | 4.3% |
| Polyethylene glycol 1000 monostearate | — | 6.0% |
| Stearic acie | — | 7.2% |
| Propyl paraben | 0.15% | 0.15% |
| Part B | | |
| Methyl paraben | 0.15% | 0.15% |
| Glycerol | 8.0% | — |
| Propylene glycol | — | 2.5% |
| Water | 43.4% | 74.0% |
| Perume | 0.3% | 0.2% |

EXAMPLE III

| Emollient Lotion, O/W Nonionic Type | | |
|---|---|---|
| | A | B |
| Part A | | |
| Chlorphenesin | 5.0% | 5.0 % |
| Lanolin | 1.0% | — |
| Cetyl alcohol | 1.0% | — |
| Arlacel 80 | 2.1% | — |
| Tween 80 | 4.9% | — |
| Velvasil Silicone Fluid 1000 | 5.0% | — |
| Light mineral oil | 35.0% | — |
| Polyethylene glycol 400 monostearte | — | 2.5% |
| Polyethylene glycol 400 distearate | — | 2.5% |
| Olive oil | — | 47.5% |
| Propyl paraben | 0.15% | 0.15% |
| Antioxidant | — | 0.05% |
| Part B | | |
| Methyl paraben | 0.15% | 0.15% |
| Water | 50.4% | 46.8% |
| Perfume | 0.3% | 0.35% |

EXAMPLE IV

| Hand Cream | A Anionic stearate type | B Anionic stearate-gum type | C Anionic nonsoap type | D Nonionic type | E Nonionic type | F Cationic-nonionic type | G Catonic-anionic type |
|---|---|---|---|---|---|---|---|
| Part A | | | | | | | |
| Chlorphenesin | 5% | 5% | 5% | 5% | 5% | 5% | 5% |
| Cetyl alcohol | 2% | — | 10% | — | — | — | — |
| Glyceryl monostearate, pure | — | — | — | — | — | 10% | — |
| Isopropyl myristate | — | — | — | — | — | — | 3% |
| Isopropyl palmitate | — | — | — | 1% | 3% | — | — |
| Lanolin | 1% | 1% | — | — | — | 2% | — |

-continued

| Hand Cream | A Anionic stearate type | B Anionic stearate-gum type | C Anionic nonsoap type | D Nonionic type | E Nonionic type | F Cationic-nonionic type | G Catonic-anionic type |
|---|---|---|---|---|---|---|---|
| Mineral oil | 2% | — | — | — | — | — | — |
| Polyethylene glycol 1000 monostearate | — | — | — | — | 5% | — | — |
| Polyethylene sorbitan monostearate | — | — | — | 1.5% | — | — | — |
| Propyl paraben | — | 0.05% | — | — | — | — | — |
| Sodium cetyl sulfate | — | — | 2% | — | — | — | — |
| Sorbitan monostearate | — | — | — | 2% | — | — | — |
| Stearic acid | 13% | 16% | 8% | 15% | 20% | — | 17% |
| Stearyl alcohol | — | — | 3% | — | — | — | — |
| Stearyl colamino formyl methyl pyridinium chloride | — | — | — | — | — | 1.5% | — |
| Part B |  |  |  |  |  |  |  |
| Glycerol | 12% | — | 8% | — | — | 15% | 10% |
| N (lauroyl colamino formyl methyl) pyridinium chloride | — | — | — | — | — | — | 5% |
| Methyl paraben | 0.15% | 0.15% | 0.1% | 0.1% | 0.15% | 0.1% | 0.1% |
| Polyethylene glycol 300 monostearate | — | — | — | — | 5% | — | — |
| Propylene glycol | — | 10% | — | — | — | — | — |
| Potassium hydroxide | 1% | 0.6% | — | — | — | — | — |
| Quinec seed mucilage (2% solution) | — | 25% | — | — | — | — | — |
| Sodium hydroxide | — | 0.1% | — | — | — | — | — |
| Sodium lauryl sulfate | — | — | 1% | — | — | — | — |
| Sorbo | — | — | — | 3.5% | 3% | — | — |
| Triethanolamine | — | 0.3% | — | — | — | — | — |
| Water | 68.85% | 46.8% | 67.9% | 76.9% | 63.85% | 71.4% | 64.9% |
| Part C |  |  |  |  |  |  |  |
| Perfume and color | q.s. | q.s. | q.s. | q.s. | q.s. | q.s. | q.s. |

EXAMPLE V

| Hand Lotion | A Anionic stearate type | B Anionic stearate-gum type | C Anionic-nonionic nonsoap type | D Nonionic-anionic type | E Nonionic type | F Cationic-nonionic type | G Cationic-anionic type |
|---|---|---|---|---|---|---|---|
| Part A |  |  |  |  |  |  |  |
| Chlorphenesin | 5% | 5% | 5% | 5% | 5% | 5% | 5% |
| Cetyl alcohol | 0.5% | 0.5% | — | — | — | — | 1.5% |
| Glyceryl monostearate | — | — | 1% | 4% | — | 1% | — |
| Isopropyl palmitate | — | — | 4% | — | — | 3% | — |
| Lanolin | 1% | — | — | — | 1% | 1% | — |
| Lanolin absorption base | — | — | — | 1% | — | — | — |
| Mineral oil | — | — | — | — | — | — | 3% |
| Polyethylene glycol 400 distearate | — | — | 2% | — | — | — | — |
| Propylene glycol monostearate | — | — | — | — | 4% | — | — |
| Nimlesterol or Amerchol L-101 | — | — | — | — | 7% | — | — |
| Stearic Acid | 3% | 5% | — | 1.5% | — | — | 2% |
| Part B |  |  |  |  |  |  |  |
| Glycerol | 2% | 2% | 10% | 3% | — | 5% | 7% |
| Methyl paraben | 0.1% | 0.1% | 0.1% | 0.1% | 0.1% | 0.1% | 0.1% |
| N (lauroyl colamino formyl methyl pyridinium chloride) | — | — | — | — | — | — | 1.5% |
| Propylene glycol | — | — | — | — | 3% | — | — |
| Sodium alginate | — | 0.3% | — | — | — | — | — |
| Sodium cetyl sulfate | — | — | 5% | — | — | — | — |
| Sodium lauryl sulfate | — | — | — | 1% | — | — | — |
| Stearyl colamino formyl methyl pyridinium chloride | — | — | — | — | — | 1.5% | — |
| Triethanolamine | 0.75% | 0.5% | — | — | — | — | — |
| Water | 92.65% | 86.6% | 77.9% | 89.4% | 84.9% | 88.4% | 84.9% |
| Part C |  |  |  |  |  |  |  |
| Ethyl alcohol | — | 5% | — | — | — | — | — |
| Color | q.s. | q.s. | q.s. | q.s. | q.s. | q.s. | q.s. |
| Perfume | q.s. | q.s. | q.s. | q.s. | q.s. | q.s. | q.s. |

EXAMPLE VI

| Aerosol Spray |  |
|---|---|
| Chlorphenesin | 4.0% |
| Stearic acid, triple pressed | 5.00% |
| Stripped coconut fatty acids | 0.77% |
| Silicone oil 200/100 | 0.50% |
| Triethanolamine | 2.00% |
| Blandol | 44.98% |
| Water | 40.00% |
| Glycerol | 2.50% |

| Aerosol Spray | |
| --- | --- |
| Perfume | 0.25% |
| Above concentrate | 90.00% |
| Propellant-12 | 10.00% |

Having regard to the foregoing disclosure, the following is claimed as the inventive and patentable embodiments thereof:

1. A process for alleviating contact sensitization or irritation which arises when an agent giving rise to contact hypersensitivity is administered topically to the skin of the animal, which comprises administering with the said agent an amount therapeutically effective to inhibit such contact hypersensitivity or specific irritation of a substituted phenoxy alkanol having the formula:

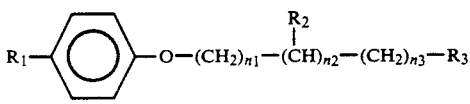

in which:

R$_1$ substituted in ortho, meta or para position or combination of these is selected from hydrogen, halogen, alkyl having from one to six carbon atoms, preferably p-chlorine or p-tertiary-butyl; and bivalent cycloalkylene condensed with the phenyl group at adjacent ring carbons thereof, such as in indane;

R$_2$ and R$_3$ are hydrogen or hydroxyl and at least one of R$_2$ and R$_3$ is hydroxyl; and n$_1$, n$_2$ and n$_3$ represent the number of CH$_2$, CHR$_2$ and CH$_2$ groups, respectively, and are numbers within the range from 1 to 10.

2. A process according to claim 1 in which the substituted phenoxy alkanol is administered together with the agent giving rise to contact hypersensitivity.

3. A process according to claim 1 in which the substituted phenoxy alkanol and the agent giving rise to contact hypersensitivity is administered separately, and in sequence.

4. A process according to claim 1 in which the substituted phenoxy alkanol is administered in the form of an emollient cream.

5. A process according to claim 1 in which the substituted phenoxy alkanol is administered in the form of a hand lotion.

6. A process according to claim 1 in which the substituted phenoxy alkanol is administered in the form of a hand cream.

7. A process according to claim 1 in which the substituted phenoxy alkanol is administered in the form of an emollient lotion.

8. A process according to claim 1 in which R$_1$ is chlorine, n$_1$, n$_2$ and n$_3$ are each 1 and R$_2$ and R$_3$ are OH.